United States Patent
Kumar et al.

(10) Patent No.: US 6,951,462 B2
(45) Date of Patent: Oct. 4, 2005

(54) DENTAL TOOL WITH RENTENTIVE FEATURE

(75) Inventors: Ajay Kumar, Palmdale, CA (US); Ines Aravena, Camarillo, CA (US)

(73) Assignee: Zimmer Dental Inc., Carlsbad, CA (US)

( * ) Notice: Subject to any disclaimer, the term of this patent is extended or adjusted under 35 U.S.C. 154(b) by 152 days.

(21) Appl. No.: 10/302,132

(22) Filed: Nov. 22, 2002

(65) Prior Publication Data

US 2003/0224325 A1 Dec. 4, 2003

Related U.S. Application Data

(60) Provisional application No. 60/385,803, filed on Jun. 4, 2002.

(51) Int. Cl.[7] .................................................. A61C 8/00
(52) U.S. Cl. ....................................... 433/174; 433/127
(58) Field of Search ................................ 433/173, 174, 433/163, 127, 128

(56) References Cited

U.S. PATENT DOCUMENTS

| | | |
|---|---|---|
| ,390,561 A | 10/1888 | Brown |
| ,732,288 A | 6/1903 | Felsch |
| ,816,828 A | 4/1906 | Smith |
| ,881,075 A | 3/1908 | Hosking |
| 1,033,049 A | 7/1912 | Van Sickle |
| 1,303,595 A | 5/1919 | Rifflard |
| 1,636,861 A | 7/1927 | Griveau |
| 1,688,670 A | 10/1928 | Swendiman |
| 1,722,893 A | 7/1929 | Burnier |
| 1,814,544 A | 7/1931 | Caimcross et al. |
| 2,151,953 A | 3/1939 | Zimmerman |
| 2,172,561 A | 9/1939 | Kruse |
| 2,253,132 A | 8/1941 | Malson |
| 2,602,727 A | 7/1952 | Warinner |
| 2,632,248 A | 3/1953 | Kohler |
| 2,667,357 A | 1/1954 | Andreasson |
| 2,704,472 A | 3/1955 | Booth |
| 2,725,632 A | 12/1955 | Rabben |
| 2,732,747 A | 1/1956 | Livermont |
| 2,743,638 A | 5/1956 | Woods |
| 2,754,591 A | 7/1956 | Schweizer |
| 2,894,759 A | 7/1959 | de Bruin |
| 2,948,173 A | 8/1960 | Herrmann |
| 3,096,659 A * | 7/1963 | Jenkins ........................ 74/157 |
| 3,165,014 A | 1/1965 | Grabovac |
| 3,191,486 A | 6/1965 | Gibbens |
| 3,274,827 A | 9/1966 | Sturtevant |
| 3,279,286 A | 10/1966 | Larson |
| 3,331,267 A | 7/1967 | Tietge |
| 3,425,314 A | 2/1969 | Ohlson |
| 3,507,043 A | 4/1970 | Rubin |
| 3,713,222 A | 1/1973 | Tofflemire |
| 3,834,026 A | 9/1974 | Klein |
| 3,921,471 A | 11/1975 | Smith |
| 3,990,438 A | 11/1976 | Pritchard |
| 4,001,940 A | 1/1977 | Cusato |

(Continued)

FOREIGN PATENT DOCUMENTS

| | | |
|---|---|---|
| DE | 42 00 364 | 9/1993 |
| DE | 195 07 535 | 9/1996 |
| EP | 0 428 490 | 4/1994 |
| EP | 0 704 281 | 8/1998 |
| WO | WO 97 47436 | 12/1997 |
| WO | WO 98/55039 | 12/1998 |

*Primary Examiner*—Ralph A. Lewis
(74) *Attorney, Agent, or Firm*—Conley Rose, P.C.

(57) ABSTRACT

A dental driving tool having a distal end with a drive mechanism adapted to drive a dental implant and a retention mechanism adapted to hold and carry the dental implant. The retention mechanism includes a housing having a ceramic locking member and corrosive resistant biasing member. Preferably, the housing is formed as an axial bore through the distal end, and the locking and biasing members are formed as a ball and spring, respectively.

29 Claims, 3 Drawing Sheets

U.S. PATENT DOCUMENTS

| | | | |
|---|---|---|---|
| 4,027,392 A | 6/1977 | Sawyer et al. | |
| 4,035,917 A | 7/1977 | Roberts | |
| 4,040,186 A | 8/1977 | Kalvelage | |
| 4,081,909 A | 4/1978 | Garcia | |
| 4,129,035 A | 12/1978 | Ango | |
| 4,177,562 A | 12/1979 | Miller et al. | |
| 4,197,647 A | 4/1980 | Goldenthal | |
| 4,215,600 A | 8/1980 | Kesselman | |
| 4,234,309 A | 11/1980 | Sellers | |
| 4,259,072 A | 3/1981 | Hirabayashi et al. | |
| 4,310,305 A | 1/1982 | Frajdenrajch | |
| 4,330,891 A | 5/1982 | Branemark et al. | |
| 4,474,089 A | 10/1984 | Scott | |
| 4,553,942 A | 11/1985 | Sutter | |
| 4,645,453 A | 2/1987 | Niznick | |
| 4,649,727 A | 3/1987 | Gray | |
| 4,655,711 A | 4/1987 | Weissman | |
| 4,682,520 A | 7/1987 | Gray | |
| 4,687,392 A | 8/1987 | Bidwell | |
| 4,712,681 A | 12/1987 | Branemark et al. | |
| 4,713,003 A | 12/1987 | Symington et al. | |
| 4,758,161 A | 7/1988 | Niznick | |
| 4,763,788 A | 8/1988 | Jorneus et al. | |
| 4,802,848 A | 2/1989 | Randin | |
| 4,833,951 A | 5/1989 | Karcher et al. | |
| 4,856,648 A | 8/1989 | Krueger | |
| 4,856,994 A | 8/1989 | Lazzara et al. | |
| 4,860,793 A * | 8/1989 | Hartl | 137/606 |
| 4,915,629 A | 4/1990 | Sellers | |
| 4,927,363 A | 5/1990 | Schneider | |
| 4,955,811 A | 9/1990 | Lazzara et al. | |
| 4,976,617 A | 12/1990 | Carchidi | |
| 4,988,297 A | 1/1991 | Lazzara et al. | |
| 4,995,810 A | 2/1991 | Soderberg | |
| 5,018,970 A | 5/1991 | Stordahl | |
| 5,026,285 A | 6/1991 | Durr et al. | |
| 5,028,181 A * | 7/1991 | Jenkins et al. | 409/215 |
| 5,064,375 A | 11/1991 | Jorneus | |
| 5,078,607 A | 1/1992 | Niznick | |
| 5,105,690 A * | 4/1992 | Lazzara et al. | 81/436 |
| 5,120,221 A | 6/1992 | Orenstein et al. | |
| 5,129,293 A | 7/1992 | Larson et al. | |
| 5,158,458 A | 10/1992 | Perry | |
| 5,167,664 A | 12/1992 | Hodorek | |
| 5,176,050 A | 1/1993 | Sauer et al. | |
| 5,180,303 A | 1/1993 | Hornburg et al. | |
| 5,197,881 A | 3/1993 | Chalifoux | |
| 5,209,659 A | 5/1993 | Friedman et al. | |
| 5,238,137 A * | 8/1993 | Cornwall | 220/327 |
| 5,281,140 A | 1/1994 | Niznick | |
| 5,282,746 A | 2/1994 | Sellers et al. | |
| 5,295,831 A | 3/1994 | Patterson et al. | |
| 5,297,963 A | 3/1994 | Dafatry | |
| 5,312,254 A | 5/1994 | Rosenlicht | |
| 5,316,476 A | 5/1994 | Krauser | |
| 5,322,443 A | 6/1994 | Beaty | |
| 5,336,090 A | 8/1994 | Wilson, Jr. et al. | |
| 5,337,638 A | 8/1994 | Coss et al. | |
| 5,338,196 A | 8/1994 | Beaty et al. | |
| 5,362,235 A | 11/1994 | Daftary | |
| 5,366,374 A | 11/1994 | Vlassis | |
| 5,366,412 A | 11/1994 | Beaty et al. | |
| 5,366,480 A | 11/1994 | Corriveau et al. | |
| 5,368,160 A | 11/1994 | Leuschen et al. | |
| 5,368,480 A | 11/1994 | Balfour et al. | |
| 5,397,269 A | 3/1995 | Beaty et al. | |
| 5,415,545 A | 5/1995 | Shaw | |
| 5,431,567 A | 7/1995 | Daftary | |
| 5,433,665 A | 7/1995 | Beaty et al. | |
| 5,437,550 A | 8/1995 | Beaty et al. | |
| 5,437,551 A | 8/1995 | Chalifoux | |
| 5,449,291 A | 9/1995 | Lueschen et al. | |
| 5,468,150 A | 11/1995 | Brammann | |
| 5,482,463 A | 1/1996 | Wilson, Jr. et al. | |
| 5,484,285 A | 1/1996 | Morgan et al. | |
| 5,538,428 A * | 7/1996 | Staubli | 433/173 |
| 5,580,246 A | 12/1996 | Fried et al. | |
| 5,582,299 A | 12/1996 | Lazzara et al. | |
| 5,622,500 A | 4/1997 | Niznick | |
| 5,630,717 A | 5/1997 | Zuest et al. | |
| 5,636,990 A * | 6/1997 | Stemmann | 433/189 |
| 5,685,204 A | 11/1997 | Braun | |
| 5,704,788 A | 1/1998 | Milne | |
| 5,725,376 A | 3/1998 | Poirier | |
| 5,733,123 A | 3/1998 | Blacklock et al. | |
| 5,734,113 A | 3/1998 | Vogt et al. | |
| 5,755,575 A | 5/1998 | Biggs | |
| 5,772,435 A * | 6/1998 | Dorman | 433/126 |
| 5,836,430 A | 11/1998 | Vasudeva | |
| 5,897,319 A | 4/1999 | Wagner et al. | |
| 5,944,525 A * | 8/1999 | Ura | 433/173 |
| 6,159,008 A * | 12/2000 | Kumar | 433/163 |
| 6,186,785 B1 * | 2/2001 | Rogers et al. | 433/141 |
| 6,206,696 B1 | 3/2001 | Day | |
| 6,217,332 B1 * | 4/2001 | Kumar | 433/173 |
| 6,261,097 B1 * | 7/2001 | Schmutz et al. | 433/173 |
| 6,280,193 B1 * | 8/2001 | Peltier | 433/174 |
| 6,398,552 B2 | 6/2002 | Rogers et al. | |
| 2002/0002881 A1 | 1/2002 | Glass | |

\* cited by examiner

DENTAL TOOL WITH RENTENTIVE FEATURE

CROSS-REFERENCE TO RELATED APPLICATIONS

This application claims benefit of priority of U.S. Provisional Application Ser. No. 60/385,803 filed Jun. 4, 2002.

FIELD OF THE INVENTION

The present invention relates generally to the field of dental implantogy and, more specifically, to an apparatus for safely and effectively carrying and then driving a dental implant in a prepared surgical site.

BACKGROUND OF THE INVENTION

In order to install a dental implant into the jawbone of a patient, the gingival tissue is incised and the bone is exposed. A series of drills are then used to form a cylindrical bore (referred as the osteotomy) in the bone. Once the osteotomy is prepared, the distal end of the implant is positioned in the bore, and a powered or manual driving tool is used to rotate and drive the implant into the osteotomy. The driving tool includes an end portion that is configured to matingly engage the end of the implant.

In some instances, a fixture mount is attached to the top of the implant with a retaining screw. The fixture mount serves as an intermediate member between the implant and driving tool. The driving tool directly engages the fixture mount and imparts torque to it to drive the implant.

The connection between the driving tool and the implant or fixture mount has several disadvantages. Often, this connection is not consistent or reliable, and the implant can loosen from the driving tool and fall off. In such a situation, the implant can be ingested or contaminated.

In some instances, a frictional fit holds the driving tool to the implant or fixture mount. The end of the driving tool may be tapered and pressed into a cavity at the coronal end of the implant to hold and drive the implant. This frictional fit, however, may wear with use and does not have even retentive forces. Further, the tight fit between the end of the driving tool and implant can deform and damage the internal cavity of the implant.

If the connection between the driving tool and implant or fixture mount is not consistent and reliable, then other problems may occur as well. For example, the posterior maxilla can have soft bone. If the connection between the driving tool and implant is too strong, then the implant can be moved or otherwise disturbed while the tool disengages from the implant. Such movement can interfere with the proper placement and location of the implant.

It would be advantageous to have dental driving that connected to the implant or fixture mount and eliminated the disadvantages of prior connections.

BRIEF SUMMARY OF PREFERRED EMBODIMENTS OF THE INVENTION

The present invention is directed toward a dental driving tool adapted to engage, carry, and drive a dental implant and dental fixture mount into the jawbone of a patient. The driving tool has a body that extends from a proximal portion to a distal portion. The distal portion has a retention mechanism that includes a housing having a biasing member and locking member located in the housing. Preferably, the housing includes an axial or radial bore that is perpendicular to a longitudinal axis of the body. The biasing member biases the locking member to slideably move in an axial or radial direction in the bore. The locking member may be formed as a ball, pin, cylinder, or the like; and the biasing member may be formed as a spring.

One advantage of the present invention is that the connection between the driving tool and the implant is consistent and reliable. As such, the likelihood that the implant will loosen from the driving tool and fall off is reduced.

The connection between the driving tool and implant is not based on a frictional taper fit but on a retention mechanism having an active or moveable locking member and biasing member. This retention mechanism will not damage the internal cavity of the implant or leave micro-fragments or residuals from the end of the driving tool.

Further, the retention mechanism and corresponding connection with the implant or fixture mount provides consistent tactile feedback while the dental driving tool disengages from the implant. A minimal or predictable amount of force is required to perform this disengagement. As such, any interference with the proper placement and location of the implant is greatly reduced, especially when the implant is placed in soft, cortical bone.

Accordingly, the present invention comprises a combination of features and advantages that overcome various problems, deficiencies, or shortcomings associated with prior devices. The various features and advantages of the invention will be readily apparent to those skilled in the art upon referring to the accompanying drawings and reading the following detailed description of the preferred embodiments of the invention.

BRIEF DESCRIPTION OF THE DRAWINGS

For a more detailed description of preferred embodiments of the present invention, reference will now be made to the accompanying drawings, wherein.

DETAILED DESCRIPTION OF PREFERRED EMBODIMENTS

Figure 1:
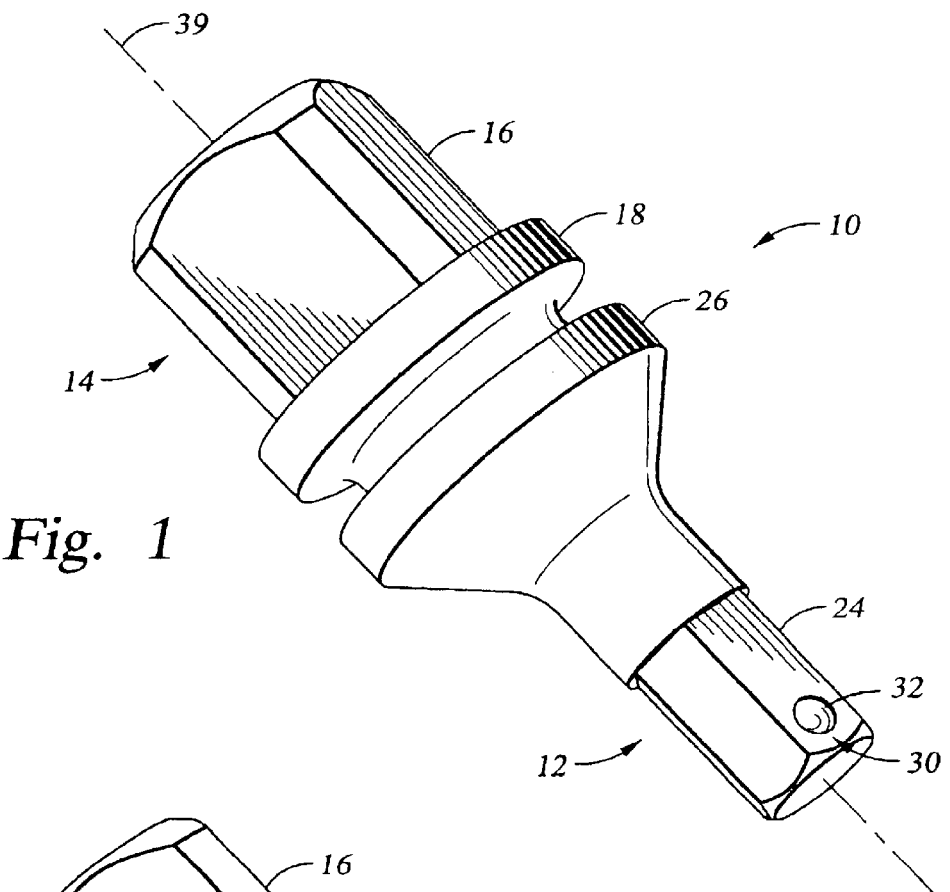
FIG. 1 is a perspective view of an assembled dental drive tool made in accordance with a preferred embodiment of the present invention.
Figure 2:
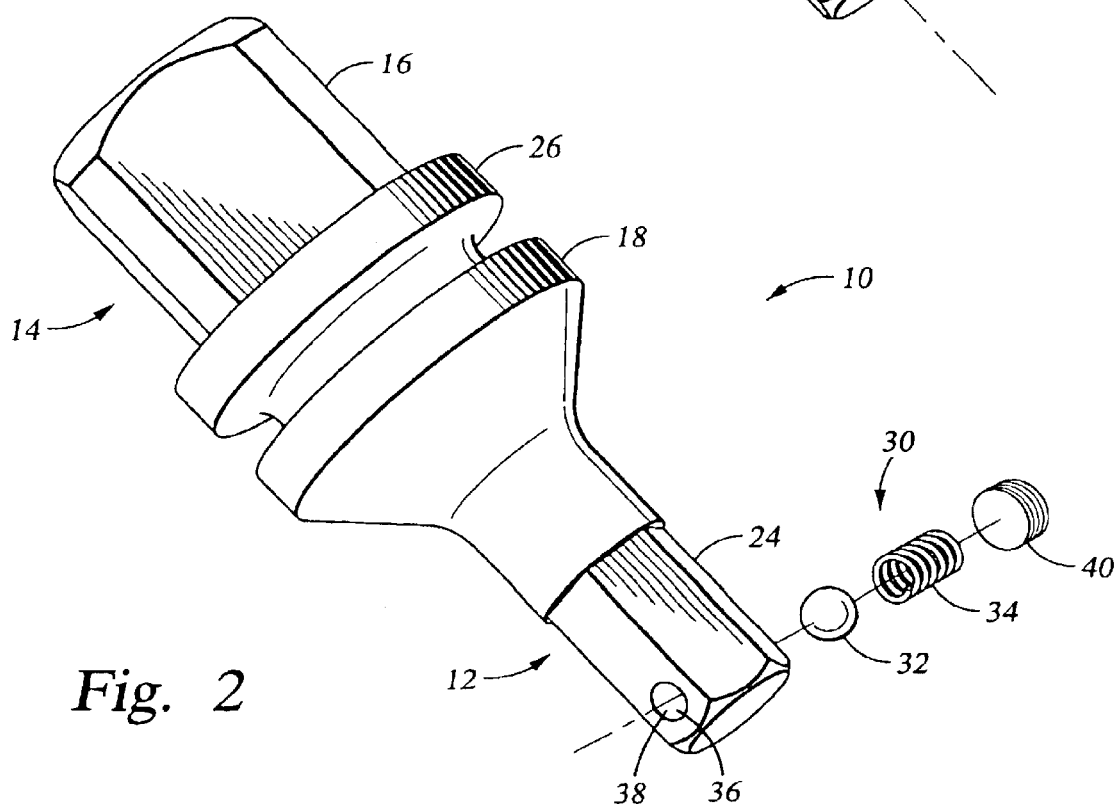
FIG. 2 is a solid view of an unassembled dental drive tool shown in FIG. 1.

FIGS. 1 and 2 show the dental drive tool 10 of the present invention. The drive tool generally has an elongated body or shaft that extends from a distal end or implant engaging end 12 to a proximal end or tool engaging end 14. The drive tool may be formed of various materials known to those skilled in the art, such as titanium, steel, polymer, or composites.

The proximal end 14 includes a hexagonal projection 16 that is adapted to connect to a motorized dental drive tool (not shown). A stop or radial flange 18 is formed at the end of the hexagonal projection 16. The proximal end may have other configurations known to those skilled in the art as well. For example, a right-angle latch lock connection or a square connection can be used.

Further, the proximal end may be configured for manually driving the driving tool 10. Specifically, a hand-grip surface (not shown) can be included at the proximal end so the drive tool 10 can be manually rotated.

The implant engaging end 12 includes an elongated drive shaft 24 having a hexagonal configuration. The shaft 24 widens and transitions to a radial flange 26 that is adjacent flange 18. A distal portion of the drive shaft 24 includes a retention mechanism 30. The retention mechanism and drive shaft are adapted to hold, carry, and drive dental implants and fixture mounts into the jawbone of a patient.

Figures 3, 4:
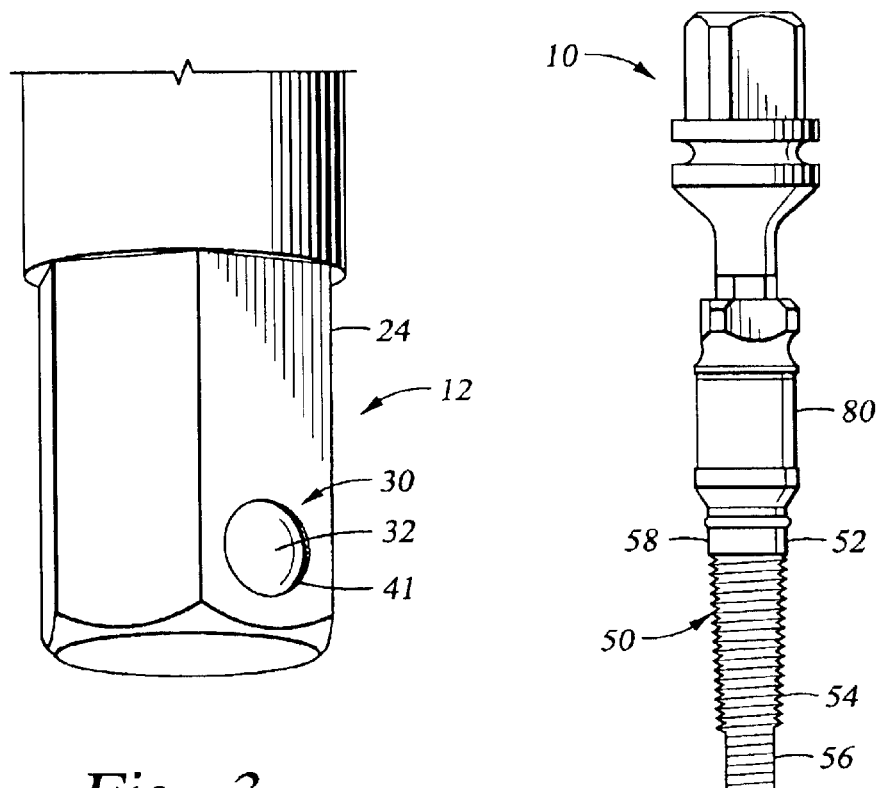
FIG. 3 is an enlarged, partial perspective view of the distal end of the drive tool of FIG. 1.
FIG. 4 is a side view of a vial, implant, and drive tool.

As shown in FIGS. 1–3, the retention mechanism includes a locking member 32 and a biasing member 34. The locking and biasing members are located in a housing 36 adjacent the end of engaging end 12. The housing may have various configurations known to those skilled in the art. As shown in FIG. 3, the housing may be an axial or radial bore 38 that extends completely through the drive shaft 24. This bore is perpendicular to a longitudinal axis 39 that extends through the body of the driving tool (see FIG. 1).

Preferably, the locking member 32 is formed as a ball, but one skilled in the art will appreciate that other locking members can be used as well, such as a pin, button, cylinder, or the like. Further, the biasing member is shown as a spring, but one skilled in the art will appreciate that other biasing members can be used as well.

As shown in FIG. 3, one end of the spring includes a stop member or plug 40 that closes one end of the bore 38 and maintains the spring in the housing. The other end of the bore remains open. A ledge 41 (shown in FIG. 3) inside bore 38 prevents the ball 32 from exiting the housing while under bias from the spring.

One skilled in the art will appreciate that various means may be employed to retain the locking and biasing member in engaging end 12. For example, bore 38 may be formed with a counterbore that has an opening smaller than the diameter of the locking member. As such, the locking member would not be able to escape the bore. As another example, the bore 38 could include stop members at each end. These stop member could be press-fit in the bore and would prevent the locking and biasing members from leaving the confines of the bore.

Figure 5:
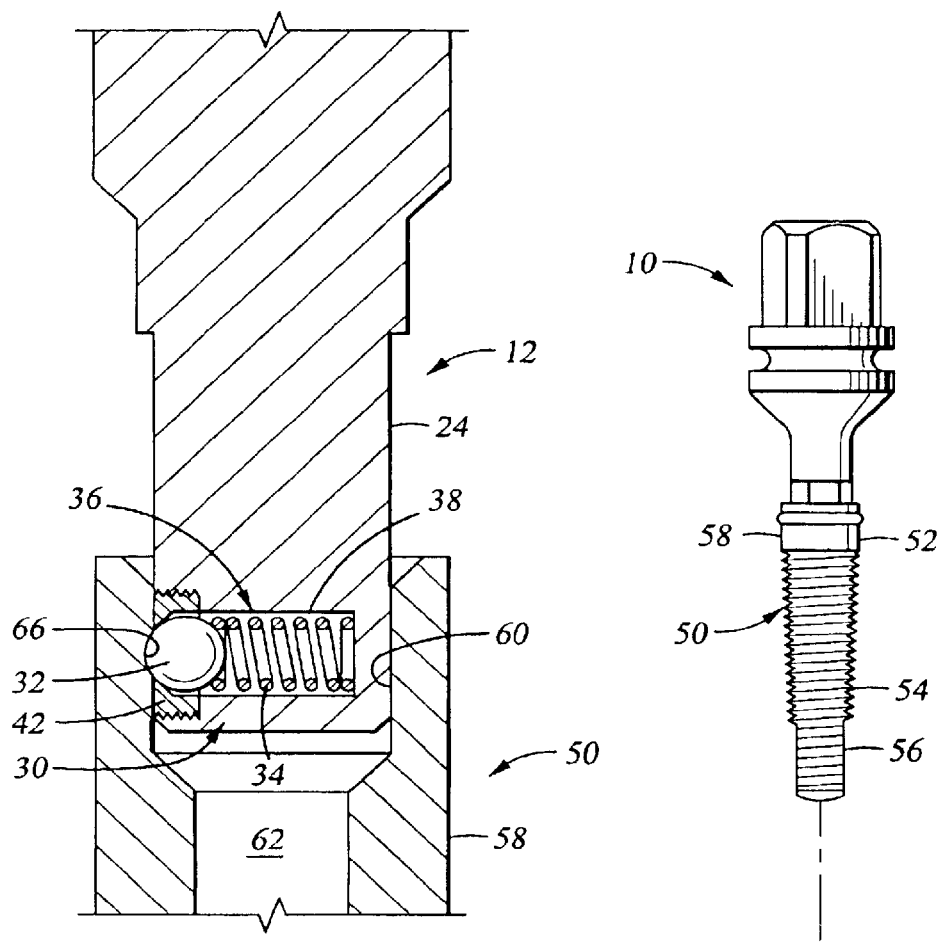
FIG. 5 is a partial, cross-sectional of the connection between the distal end of the drive tool and the coronal end of the implant of FIG. 4.

FIG. 5 shows another example for housing the locking member and biasing member. In this figure, the housing is a cylindrical bore that partially extends into the engaging end of the driving tool. The biasing member 34 biases the locking member 32 outwardly toward the exterior surface of the drive shaft 24. A stop 42 keeps the locking member 32 inside the housing.

Figure 6:
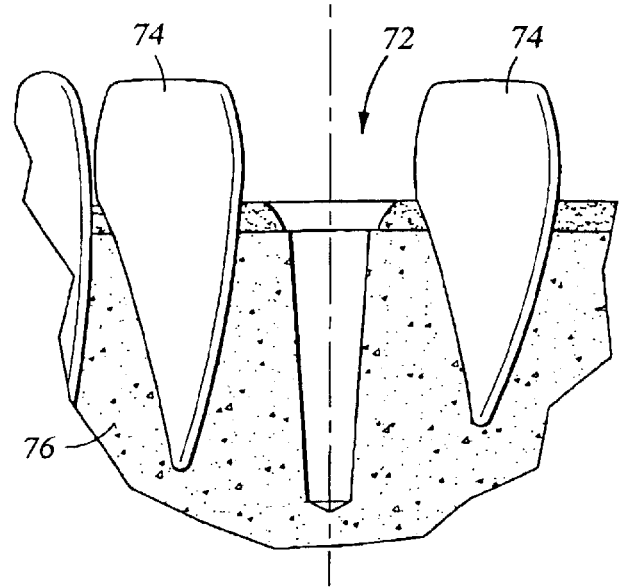
FIG. 6 is a side view of a drive tool attached to a implant being placed in an osteotomy of a human jawbone.

As shown in FIGS. 4–6, the drive tool is adapted to engage, hold, carry, and drive a dental implant 50. The implant 50 preferably is made of titanium or another strong and biocompatible metal and includes a generally cylindrical body 52 having external threads 54, tapered end 56 and coronal end 58 for engaging with the distal end of the drive tool. Coronal end 58 of implant 50 includes an engaging feature 60 adapted to engage the distal end of the drive tool. This engaging feature can be various configurations known to those skilled in the art, such as splines, external or internal hexagon, octagon, star, polygons, or other geometries or retention mechanisms. A central bore 62 is located adjacent the engaging feature to engage corresponding threads of retaining screw (not shown).

As best shown in FIG. 5, the biasing member 34 biases the locking member 32 against the coronal end of the implant to hold and carry the implant. Specifically, the locking member is biased against an internal wall 66 of the engaging feature 60. The retention mechanism thus holds and carries the implant. Preferably, the retention mechanism releasably holds the implant with a removal force of about one ounce to 1½ pounds.

As shown in FIGS. 4 and 6, the removal force enables the drive tool 10 to remove the implant 50 from its packaging, here a vial 70. The implant is then transported from the vial to the osteotomy site 72 located between two teeth 74 in a jawbone 76 of a patient. Once the implant is positioned at the osteotomy, the drive tool is rotated and the implant is driven into the bone. The distal end of the drive tool transfers torque from the drive tool to the engaging feature 60 of the implant. As shown in FIG. 4, the distal end of the drive tool can also engage a fixture mount 80 located between the drive tool 10 and implant 50.

Preferably, the locking member 32 is a ball and is formed of hard material, such as ceramic, ruby, or silicone nitride. One advantage of the present invention is that the ceramic ball will not leave a residue or deposit on the surface of the implant where the implant and ball contact.

Preferably, the biasing member is a spring and is formed of a biocompatible, corrosive resistant material, such as titanium. Other materials include stainless steel (such as SS 17-4) coated with an amorphous diamond coating or a chromium coating. One advantage of the present invention is that the spring is biocompatible and will not corrode.

Another advantage of the present invention is that the connection between the driving tool and the implant is consistent and reliable. This connection is not based on frictional taper fit but on a retention mechanism having an active or moveable locking member and biasing member. The biasing member biases the locking member to slideably move in an axial bore located in the driving tool. This retention mechanism will not damage the internal cavity of the implant, leave micro-fragments or residuals from the end of the driving tool, and provides a consistent connection force with the implant. Further, the likelihood that the implant will loosen from the driving tool and fall off is reduced.

Further, the retention mechanism and connection with the implant or fixture mount provides consistent tactile feedback while the dental driving tool disengages from the implant. A minimal or predictable amount of force is required to perform this disengagement. As such, any interference with the proper placement and location of the implant is greatly reduced, especially when the implant is placed in soft, cortical bone, such as in the posterior maxilla.

It will be appreciated that the present invention could incorporate multiple locking members and biasing members. Two balls, for example, could be employed in the same bore, with one ball at the first end of the spring and a second ball at the other end. Multiple stop members could be placed at the ends of the bore to prevent the balls from exiting the bore. Further, multiple bores could be used to house multiple balls and springs.

Further yet, the present invention can be used with various dental tools, implants, and accessories. The retention mechanism, for example, can be employed with an abutment, fixture mount, or other driving apparatus.

As understood by those skilled in the art, the precise configuration and dimensions of the various components of drive tool may vary depending upon the size of the implant or device to be installed. For example, a number of conventional implants are constructed so as to have either a polygonal extension or a polygonal socket at the coronal end of the implant. The principles of the present invention can be applied so the retention mechanism is fabricated with a socket type connection at the end of the distal end. The locking member would partially protrude in the socket to engage a protrusion from the coronal end of the implant. For example, a hexagonal socket would matingly engage a correspondingly sized and shaped hexagonal projection on the coronal end of an implant or on the end of a fixture mount.

While preferred embodiments of this invention have been shown and described, modifications thereof can be made by one skilled in the art without departing from the spirit or teaching of this invention. The embodiments described herein are exemplary only and are not limiting. Many variations and modifications of the system, apparatus, and methods are possible and are within the scope of the inventions claimed below. Accordingly, the scope of protection is not limited to the embodiments described herein, but is only limited by the claims that follow, the scope of which shall include all equivalents of the subject matter of the claims.

What is claimed is:

1. A dental tool, comprising:
   a shaft having a distal end and a proximal end, wherein the distal end is adapted to drive a dental implant into a jawbone;
   a retention mechanism located at the distal end and including a ball and spring biasing the ball, wherein the retention mechanism is adapted to hold and carry the dental implant;
   wherein the ball and spring are housed in an axial bore, and the spring biases the ball against an internal cavity of the dental implant; and
   wherein the ball is formed of a ceramic and the spring is formed of a corrosive resistant metal.

2. The dental tool of claim 1 wherein the ball is formed of one of ruby or silicone nitride, and the spring is formed of one of titanium or steel with a diamond or chromium coating.

3. The dental tool of claim 2 wherein the retention mechanism holds the dental implant with a force of about one ounce to 1½ pounds.

4. The dental tool of claim 3 wherein the distal end is shaped as one of a hexagon, star, triangle, square, or octagon.

5. A dental tool adapted to engage, carry, and drive a dental implant, the driving tool comprising:
   an elongated shaft having proximal and distal ends;
   a housing located at the distal end;
   a locking member and a biasing member located in the housing for biasing the locking member against a surface of the implant to hold and carry the implant;
   wherein the locking member is formed of a ceramic and the biasing member is formed of a corrosive resistant metal.

6. The dental tool of claim 5 in which the locking member is formed of ruby or silicone nitride.

7. The dental driving tool of claim 6 in which the biasing member is formed of titanium.

8. The dental driving tool of claim 7 in which the distal end has a polygonal shape adapted to engage and drive the implant into a jawbone.

9. The dental driving tool of claim 8 in which the locking member and biasing member hold the dental implant with a removal force between one ounce and 1½ pounds.

10. A dental tool, comprising:
    a shaft having a distal end and a proximal end;
    a drive mechanism located at the distal end, wherein the drive mechanism is adapted to drive a dental implant into a jawbone;
    a retention mechanism located at the distal end and including a housing, a locking member, and a biasing member biasing the locking member, wherein the locking member and biasing member are located in the housing and adapted to hold the dental implant; and
    wherein the locking member is formed of ceramic as one of a ball, pin, or cylinder;
    and the biasing member is a spring formed of a corrosive resistant material.

11. The dental tool of claim 10 in which the housing includes an axial bore that is perpendicular to a longitudinal axis that extends through the shaft.

12. The dental driving tool of claim 11 in which the locking member and biasing member are removable from the housing.

13. The dental driving tool of claim 12 in which the drive mechanism has a polygonal configuration that matches a polygonal configuration at a coronal end of the implant.

14. The dental driving tool of claim 11 in which the locking member slideably moves in the axial bore.

15. The dental driving tool of claim 14 in which the locking member partially protrudes from the axial bore and engages a surface of the dental implant.

16. A dental tool, comprising:
    a shaft having a distal end and a proximal end, wherein the distal end is adapted to drive a dental implant into a jawbone;
    a retention mechanism located at the distal end and including a ball and spring biasing the ball, wherein the retention mechanism is adapted to hold and carry the dental implant;
    wherein the ball and spring are housed in an axial bore, and the spring biases the ball against an internal cavity of the dental implant; and
    wherein the ball is formed of ruby and the spring is formed of titanium.

17. The dental tool of claim 16 wherein the retention mechanism holds the dental implant with a force of about one ounce to 1½ pounds.

18. The dental tool of claim 16 wherein the distal end is shaped as one of a hexagon, star, triangle, square, or octagon.

19. The dental tool of claim 16 wherein the ball and spring are housed in an axial bore;
    the spring biases the ball against an internal cavity of the dental implant; and
    the distal end has a polygonal shape adapted to engage and drive the implant into a jawbone.

20. A dental tool adapted to engage, carry, and drive a dental implant, the driving tool comprising:
    an elongated shaft having proximal and distal ends:
    a housing located at the distal end;
    a locking member and a biasing member located in the housing for biasing the locking member against a surface of the implant to hold and carry the implant;
    wherein the locking member is formed of ruby and the biasing member is formed of titanium.

21. The dental tool of claim 20 wherein the distal end has a polygonal shape adapted to engage and drive the implant into a jawbone.

22. The dental tool of claim 20 wherein the distal end has a polygonal shape adapted to engage and drive the implant into a jawbone and the retention mechanism holds the dental implant with a force of about one ounce to 1½ pounds.

23. The dental tool of claim 20 wherein the locking member and biasing member are housed in an axial bore, and the biasing member biases the locking member against an internal cavity of the dental implant.

24. A dental tool, comprising:
- a shaft having a distal end and a proximal end;
- a drive mechanism located at the distal end, wherein the drive mechanism is adapted to drive a dental implant into a jawbone;
- a retention mechanism located at the distal end and including a housing, a locking member, and a biasing member biasing the locking member, wherein the locking member and biasing member are located in the housing and adapted to hold the dental implant; and
- wherein the locking member is formed of ruby as one of a ball, pin, or cylinder; and the biasing member is a spring formed of titanium.

25. The dental tool of claim 24 wherein the housing includes an axial bore that is perpendicular to a longitudinal axis that extends through the shaft.

26. The dental tool of claim 25 wherein the locking member slideably moves in the axial bore.

27. The dental tool of claim 26 wherein the locking member partially protrudes from the axial bore and engages a surface of the dental implant.

28. The dental tool of claim 24 wherein the locking member and biasing member are removable from the housing.

29. The dental tool of claim 24 wherein the drive mechanism has a polygonal configuration that matches a polygonal configuration at a coronal end of the implant.

* * * * *